United States Patent [19]
Lee et al.

[11] Patent Number: 5,807,943
[45] Date of Patent: Sep. 15, 1998

[54] SYNTHESIS OF GLYCOPOLYMERS

[75] Inventors: Yuan-Chuan Lee; Jian-Qiang Fan, both of Baltimore, Md.

[73] Assignee: Johns Hopkins University, Baltimore, Md.

[21] Appl. No.: 838,132

[22] Filed: Apr. 15, 1997

Related U.S. Application Data

[62] Division of Ser. No. 445,865, May 22, 1995, Pat. No. 5,663,254.

[51] Int. Cl.$^6$ .......................... C12P 19/00; C08G 63/48; C08G 63/91

[52] U.S. Cl. ........................................ 526/238.2; 525/54.2

[58] Field of Search ......................... 526/238.2; 525/54.2

[56] References Cited

PUBLICATIONS

Derwent Abstracts 95–135909/18, "Production of Sugars and Complex Carbohydrates," Kirin Brewery Company, (Mar., 1995).

Derwent Abstracts 93–136759/17, "Glucide or Complexed Glucide Preparation for Sugar Chain Remodeling," Takara Shuzo Company (Mar., 1993).

Takegawa et al., "Synthesis of Neoglycoproteins Using Oligosaccharide–transfer Activity with Endoβ–N–Acetylglucosaminidase," vol. 270, No. 7, Issue of Feb. 17, pp. 3094–3099 (1995).

*Primary Examiner*—Frederick Krass
*Attorney, Agent, or Firm*—Cushman Darby & Cushman IP Group of Pillsbury Madison & Sutro

[57] ABSTRACT

Neoglycoconjugates and new intermediates for the synthesis thereof are synthesized by use of Endo-β-N-acetylglucosaminidase from *Arthrobacter protophormiae* (Endo-A) in a medium containing an organic solvent.

6 Claims, 9 Drawing Sheets

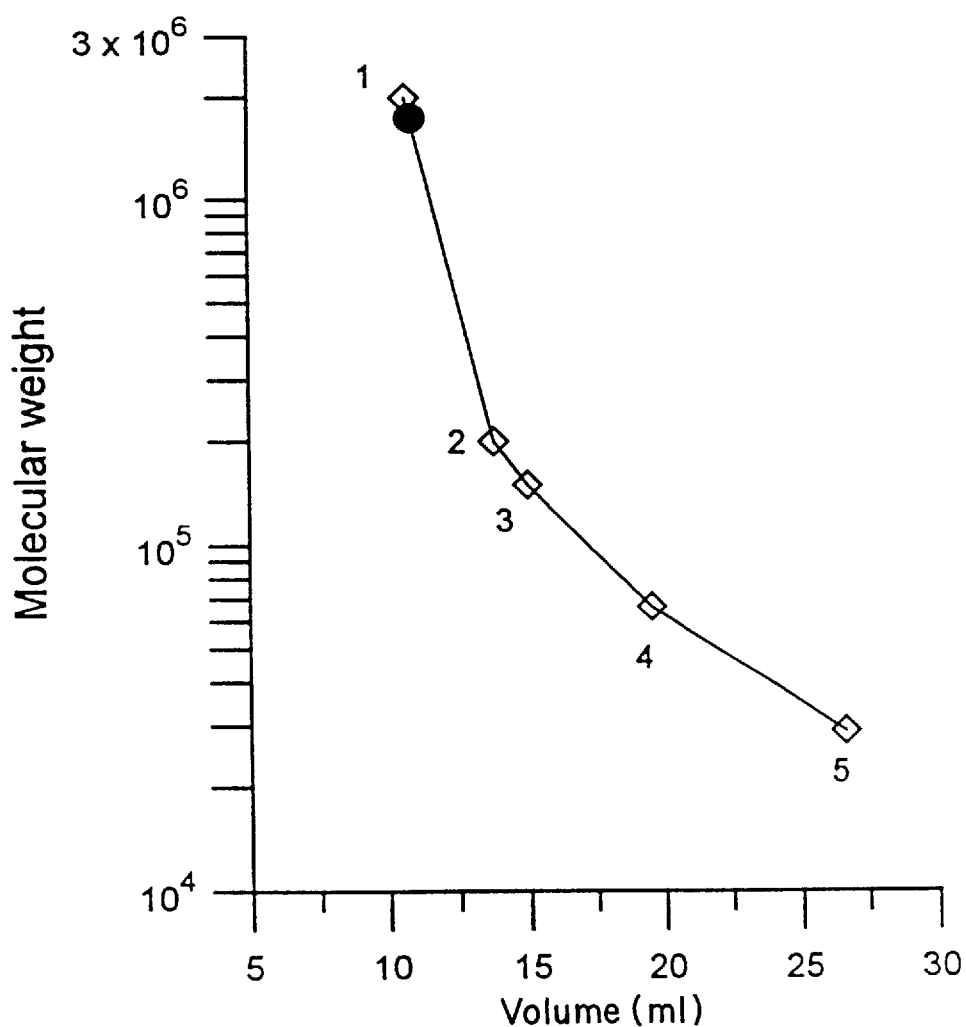

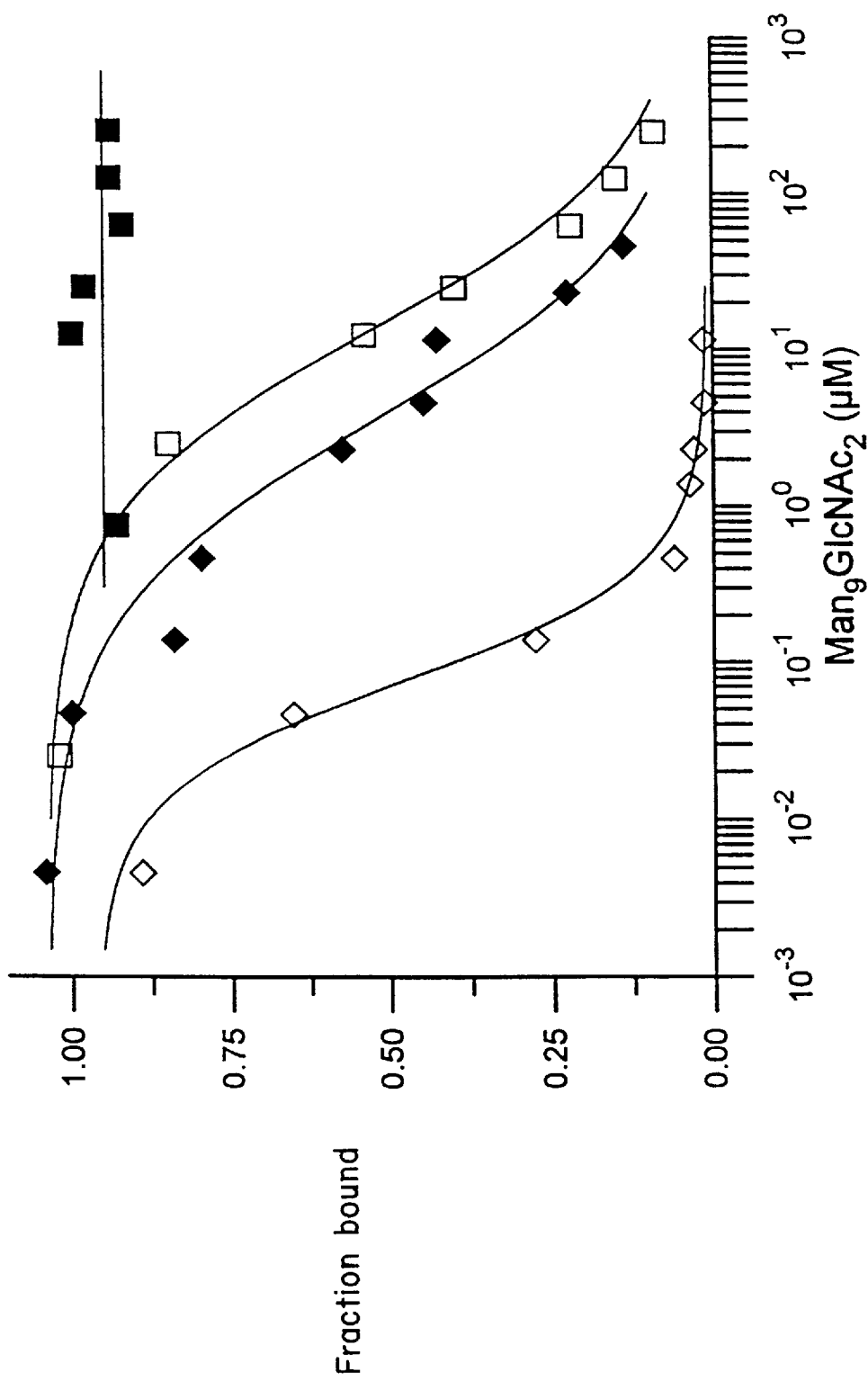

SYNTHESIS OF GLYCOPOLYMERS

This application is a divisional of U.S. Ser. No. 08/445,865 filed May 22, 1995 which is now U.S. Pat. No. 5,663,254.

BACKGROUND OF THE INVENTION

1. Field of the Invention

The present invention relates to glycopolymers and to methods and compositions for synthesizing glycopolymers. More particularly, it relates to use of Endo-β-N-acetylglucosaminidase from *Arthrobacter protophormiae*, to produce neoglycoconjugates containing high-mannose type chains.

2. Background Information

Carbohydrates possess important biological functions, such as cell-cell recognition (Wassarman, 1991; Patankar et al, 1993; and Lasky et al., 1992), lectin binding (Lee, 1988; and Lee et al., 1991, *Pure & Appl. Chem.*), viral infection (Glick et al., 1991; and Toogood et al., 1991). Studies of carbohydrate functions require structurally well-defined and highly pure compounds which are usually difficult to obtain from the natural sources. Consequently, synthesis and construction of neoglycoconjugates (proteins, lipids and other types of compounds that have been derivatized with mono- or oligosaccharides) have rapidly gained attention during the past decade (Lee, 1994). Chemical syntheses of neoglycoconjugates have been aggressively developed, but they usually involve multiple, laborious steps. Synthesis of high mannose type oligosaccharides has proven to be especially difficult, even with enzymatic methods.

Endo-β-N-acetylglucosaminidase from *Arthrobacter protophormiae* (Endo-A) is a glycosidase which performs both hydrolytic and transglycosylation functions. This enzyme cleaves the glycosidic bond in the core GlcNAcβ1,4GlcNAc residues of high mannose type and hybrid type N-linked sugar chains in glycoprotein (Takegawa et al., 1989) and also transfers oligosacharide to some mono- and disaccharides (Takegawa et al., 1991a, 1991b). (High mannose type compounds are compounds with only 2-acetylglucosamine residues immediately adjacent to the asparagine, with the remainder of the chain being branched and usually consisting of mannose only, although further modifications with xylose and fucose are sometimes seen. A complex type compound is one consisting of N-acetylglucosamine, galactose, and sometimes fucose and sialic acids. A hybrid type compound is a hybrid of the two.)

The efficiency of the transglycosylation reaction can be markedly increased by addition of organic solvents such as acetone, dimethyl sulfoxide (DMSO) and N,N-dimethyl formamide (DMF), to the reaction solution. For example, when transglycosylation activity of Endo-A is measured using $Man_9$-$GlcNAc_2Asn$ as the donor and GlcNAc as acceptor, the ratio of transglycosylation to hydrolysis is 1:2 in aqueous medium, but when 30% acetone is added, transglycosylation will be performed to near completion. This characteristic makes it possible to synthesize novel glycosides and neoglycoconjugates with high efficency and purity.

Using this method we have synthesized several functional intermediates for neoglycoconjugates, one of which was converted into a glycopolymer with pendant $Man_9GlcNAc_2$ chains. The glycopolymer thus prepared displays a drastically greater inhibition of binding by mannose-binding protein from liver over the monomer oligosaccharide.

SUMMARY OF THE INVENTION

This invention provides neoglycoconjugates and new functional intermediates for neoglycoconjugates synthesized by means of Endo-A in reaction, mixtures containing organic solvent.

This invention further provides synthetic high mannose type and hybrid type glycopolymers that have a high degree of purity.

This invention further provides a glycopolymer with pendant $Man_9GlcNAc_2$ chains with much greater inhibition of mannose binding protein (MBP) from liver than the monomer oligosaccharide.

This invention still further provides a method of synthesizing neoglycocongugates and their functional intermediates.

BRIEF DESCRIPTION OF THE DRAWINGS

FIG. 7. Determination of molecular weight of the glycopolymer by HPGFC. HPGFC was performed with a size exclusion column (7.5×600 mm) and 0.1M phosphate buffer (pH 7.0) containing 0.3M NaCl as an eluent at a flow rate of 1.0 ml/min. Effluent was monitored by absorbance at 220 nm. O: glycopolymer; ◇: reference compounds; 1: Blue dextran (2,000,000); 2: B-amylase (200,000); 3: alcohol dehydrogenase (150,000); 4: albumin bovine serum (66,000) and 5: carbonic anhydrase (29,000).

FIG. 8. Inhibition of binding by serum- and liver-MBP-CRDs by the glycopolymer. The fitted curves were obtained using the program ALLFIT (De Lean et al., 1978). Concentrations of SBA and glycopolymer are expressed on the bases of $Man_9GlcNAc_2$. ■: SBA+serum MBP-CRD; □: SBA+liver MBP-CRD; ♦: glycopolymer+serum MBP-CRD; ◇: glycopolymer+liver MBP-CRD.

DETAILED DESCRIPTION OF THE INVENTION

Materials and Methods

Figure 1B:
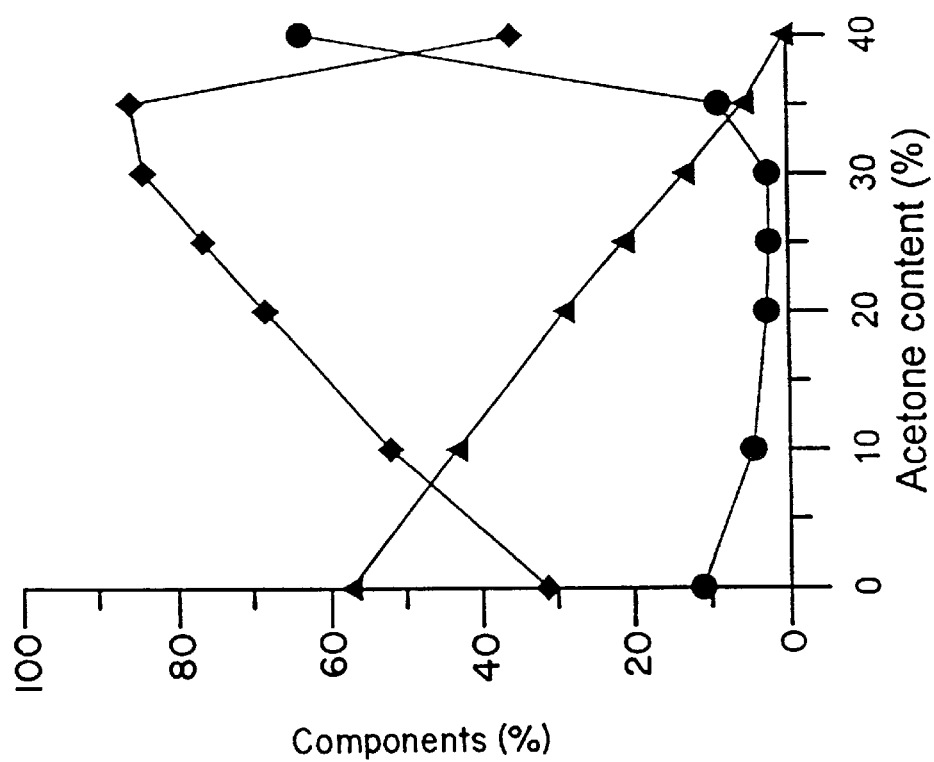
FIGS. 1A and 1B. Optimization of Endo-A transglycosylation conditions. The optimum levels of the enzyme (A) and the acetone content (B) for transglycosylation were determined by the reactions carried out in a mixture of 11.6 nmol $Man_9GlcNAc_2Asn$ (donor), 4 μmol GlcNAc-NAP (acceptor) and various amounts of the enzyme (A) or 2.2 mU enzyme (B) in 10 μl of 10 mM ammonium acetate buffer (pH 6.0) containing 30% acetone (A) or different concentrations of acetone (B). The reaction mixtures were incubated at 37° C. for 15 min and the products were analyzed with HPAEC-PAD. (O): substrate; (♦): transglycosylation product; (▲): hydrolytic product.

The following abbreviations are used in the specification:
Bn: benzyl; BSA: bovine serum albumin; CRD: carbohydrate recognition domain; DMF: N,N-dimethyl formamide; DMSO: dimethyl sulfoxide; Endo-A: Endo-β-N-acetyl-D-glucosaminidase from *Arthrobacter protophormiae;* GlcNAc: N-acetyl-D-glucosamine; $^1$H-NMR: $^1$H-nuclear magnetic resonance spectroscopy; HPAEC-PAD: high performance anion exchange chromatography with pulsed amperometric detector; HPLC: high performance liquid chromatography; HPGFC: high performance gel filtration chromatography; Man: mannose; MBP: mannose-binding protein; 4mU: 4-methylumbelliferyl; NAP: 3-(N-acryloylamino)propyl; pNP: p-nitrophenyl; SBA: soybean agglutinin.

All monosaccharides used are of the D-configuration.

EXPERIMENTAL PROCEDURES

Materials

Endo-A was purified as described by Takegawa et al. (1989). $Man_9GlcNAc_2Asn$ was prepared from soybean agglutinin by exhaustive Pronase digestion, followed by gel filtration on Sephadex G-50 and further HPLC purification using a graphitized carbon column (Fan et al., 1994). Glycoamidase A was from Seikagaku America, Inc. (Rockville, Md.). GlcNAc was purchased from Pfanstiehl Laboratories, Inc. (Waukegan, Ill.). 3-(N-acryloylamino)-propyl β-D-GlcNAc (GlcNAc-NAP) and GlcNAc-O-$(CH_2)_3CH=CH_2$ were gifts from Dr. Shin-Ichiro Nishimura of Hokkaido University, Japan. These can be synthesized using the procedures described by Nishimura et al. (1990) and Nishimura et al. (1994a). Benzyl β-GlcNAc, 4-methylumbelliferyl β-GlcNAc, p-nitrophenyl β-GlcNAc, GlcNAc-S-$(CH_2)_6NH_2$, GlcNAc-O-$CH_2CH=CH_2$, GlcNAc-O$(CH_2)_3$NHCOCH=$CH_2$, GlcNAc-S-$CH_2$CN, GlcNAc-S-$(CH_2)_3CH_3$, (GlcNAc-S-$CH_2CH_2CH_2)_2$ and GlcNAc-S-$CH_2$CONHCH$_2$CH(OMe)$_2$ were synthesized in this laboratory as described by Lee et al. (1992). Recombinant rat MBP-CRDs from serum and liver were expressed and purified according to the method of Quesenberry and Drickamer (1992) using expression plasmid-bearing bacterial strains which were gifts from Dr. Kurt Drickamer of Columbia University.

Methods

Enzymatic reaction.

A typical enzyme reaction for transglycosylation was performed in a mixture of 3 nmol $Man_9GLcNAc_2Asn$, 4 μmol acceptor and 0.9 mU of Endo-A in a total volume of 20 μl with 25 mM ammonium acetate buffer (pH 6.0) containing 30% acetone. (Other organic solvents such as DMSO and DMF can also be used, with concentrations adjusted by routine experimentation to optimize the reaction.) After incubation at 37° C. for 15 min, the reaction was terminated by boiling for 3 min. in a water bath. The buffer was removed with a Speedvac using a vacuum pump. The reaction mixture was analysized using an HPAEC-PAD system (see below).

High performance anion exchange chromatography (HPAEC).

An HPAEC system consisting of a Bio-LC (Dionex Corp., Sunnyvale, Calif.) equipped with a pulsed amperometric detector (PAD-II) was used for analysis of the reaction products. The chromatographic data were analyzed using an AI-450 chromatography software (Dionex). The Endo-A reaction products were separated using a Dionex CarboPac PA-I column (4×250 mm) eluted at a flow rate of 1.0 ml/min with 100 mM sodium hydroxide and a gradient of sodium acetate from 30 mM to 80 mM developed in 30 min. Between runs the column was washed for 5 min. with a solution of 100 mM sodium hydroxide/200 mM sodium acetate and allowed to equilibrate for 15 min. The PAD sensitivity was set at 1K. The quantitative determination of $Man_9GlcNAc$ and $Man_9GlcNAc_2$ was carried out by comparison with standard materials obtained by complete digestion of $Man_9GlcNAc_2Asn$ by Endo-A and $Man_9GlcNAc_2AsnPhe$ by Glycoamidase A. The quantity of transglycosylation products using acceptors other than N-acetyl-glucosamine was estimated by subtraction of the remaining substrate and hydrolysis product from the starting substrate.

Transglycosylation by Endo-A using GlcNAc-NAP as acceptor

A mixture consisting of 5.8 μmol of $Man_9GlcNAc_2Asn$, 2 mmol of GlcNAc-NAP and 1.1 U of enzyme in 5 ml of 10 mM $NH_4OAc$ buffer (pH 6.0) containing 35% of acetone was incubated at 37° C. for 15 min. After stopping the reaction by placement in a boiling water bath for 3 min., the sample was applied to a Sephadex G-25 column (2×140 cm), and eluted with 0.1M acetic acid. The effluent was monitored by uv absorption at 229 nm, and the neutral sugar was determined by the phenol sulfuric acid method (McKelvy and Lee, 1969). The fractions containing high molecular weight materials were combined and lysophilized to yield 10.5 mg white powder.

Preparation of glycopolymer having pendant chains of high mannose type oligosaccharide The white powder obtained from gel filtration was used as starting material for polymerization without further purification. A small amount of the white powder (7.2 mg, ca. 3.25 μmol $Man_9GlcNAc_2$-NAP) was dissolved in 0.3 ml $H_2O$, followed by deaeration with a water aspirator for 30 min. Acrylamide (8.4 mg, 118 pmol), ammonium persulfate (APS, 0.14 μmol) and N,N,N',N'-tetramethylethylenediamine (TEMED, 6.6 μmol) were added, and the mixture was stirred at room temperature for three days, during which time, the same amounts of APS and TEMED were added to the reaction mixture daily for 2 days, and the reaction was finally completed by incubation of the mixture at 55° C. for 3 hr. The reaction mixture was applied to a column (2.5×90 cm) of Sephadex G-50 and eluted with $H_2O$. The fractions containing the glycopolymer were combined and lyophilized to obtain 5.3 mg of white powder.

Estimation of molecular weight of the glycopolymer by HPGFC

The HPGFC was performed with a Gilson HPLC system equipped with a size exclusion column (TSK-Gel G2000SW, 7.5×600 mm, TosoHaas, ND and a UV detector (Model $V_4$, ISCO). The eluent was 0.1M phosphate buffer (pH 7.0) containing 0.3M NaCl and the effluent was monitored at 220 nm. The standard compounds for molecular weight estimation were i) blue dextran (MW=2,000,000); ii) β-amylase (MW=200,000); iii) alcohol dehydrogenase (MW=150,000); iv) bovine serum albumin (MW=66,000) and v) carbonic anhydrase (MW=29,000).

MBP binding of the glycopolymer

The solid-phase binding studies were carried out essentially as described by Quesenberry and Drickamer (1992), with some minor modifications. All steps were carried out at 4° C. Briefly, CRD (50 μl) was coated onto individual polystyrene wells (Immulon 4 Removawell Strips by Dynatech, from Fisher Scientific). After incubating overnight, a blocking solution of 1% BSA in 1.25M NaCl/25 mM $CaCl_2$/25 mM Tris (pH 7.8) was added and allowed to react for 2 hours. Ligands and inhibitors were in 0.5% BSA in the above Tris buffer for binding and inhibition. The reference ligand used was $^{125}$I-[mannose$_{30}$-BSA] (ca. 2000 cpm/μg), radiolabelled by the Choloramine T method (Lee et al., 1991, *J. Biol. Chem.*) Approximately 500 cpm/well reference ligand was incubated for 20 hr with or without inhibitors at various concentrations. The well contents were then removed, washed, and counted in a Packard Minaxi gamma counter. Counts were corrected for background (counts remaining in a blocked well which was not coated with CRD), and the data were analyzed using the program ALLFIT (De Lean et al., 1978) to determine $I_{50}$ values (concentration of test ligand required for 50% inhibition) using a logistic equation for curve fitting.

$^1$H Nuclear magnetic resonance spectroscopy

300 MHz NMR spectra were recorded on a Bruker AMX 300 spectrometer and measurement of a 600 MHz NMR was performed on a Bruker AM-600 spectrometer. The chemical shifts were based on acetone (δ=2.225 ppm) as an internal standard. The samples were prepared by three cycles of dissolving in $D_2O$ and lyophilizing followed by dissolving the residue in 0.5 ml of high purity $D_2O$ (99.96% D) immediately before measurement. The 300 MHz data were recorded at 25° C. and the 600 MHz data at 60° C.

RESULTS

Transglycosylation of Endo-A to water-miscible alcohols

The transglycosylation by Endo-A using $Man_9GlcNAc_2Asn$ as donor to various water-miscible alcohols was tested. The reactions in Table 1 were carried out in 20 μl of 25 mM ammonium acetate buffer (pH 6.0) with 30% of alcohol (v/v) containing 3 nmol $Man_9GlcAc_2Asn$ (donor) and 3 mU enzyme at 37° C. for 10 min. The products were determined by HPAEC using $Man_9GlcNAc$ and $Man_9GlcNAc_2$ as reference compounds.

TABLE 1

| Transglycosylation of $Man_9GlcNAc$ to alcohols by endo-A | | |
|---|---|---|
| Alcohol (30% v/v) | Hydrolysis[a] (%) | Transglycosylation[a] (%) |
| $H_2O$ | 94.1 | 0.0 |
| MeOH | 33.2 | 64.0 |
| EtOH | 45.5 | 46.9 |
| PrOH | 4.5 | 8.0 |
| iPrOH | 72.4 | 9.6 |
| Allyl alcohol | 0.0 | 0.0 |
| Glycerol | 27.8 | 56.5 |

[a]Based on the starting donor substrate.

As can be seen in the Table, the enzyme transferred oligosaccharide to MeOH and EtOH with 64% and 47% yield, respectively, with hydrolysis levels of 33% and 46%. The anomeric configuration of the product with MeOH was found to be β by $^1$H-NMR (data not shown). PrOH (8% yield) and iso-PrOH (10% yield) could also serve as acceptors of transglycosylation, but allyl alcohol could not function as an acceptor. The enzyme appeared stable in 30% MeOH and EtOH, but unstable in 30% PrOH and allyl alcohol, (the total enzyme activities [combined hydrolysis and transglycosylation activities] in MeOH and EtOH were shown to be similar to that in $H_2O$, but much lower in the higher alcohols.) Glycerol was found to be as good an acceptor as MeOH or EtOH, with the transglycosylation yield as high as 57%.

Transglycosylation of Endo-A to various GlcNAc glycosides.

The transglycosylation of Endo-A to some functionalized GlcNAc glycosides was efficient as shown in Table 2. When acceptor concentration was 0.2M, Endo-A transferred $Man_9GlcNAc$ to $GlcNAc-O-(CH_2)_6NH_2$ (93% of the converted substrate), $GlcNAc-O-CH_2CH=CH_2$ (99%), $GlcNAc-O-(CH_2)3CH=CH_2$ (90%) and $GlcNAc-O-(CH_2)_3NHCOCH=CH_2$ (78%) with yields of 81%, 81%, 84% and 70% of the starting substrate, respectively. The reactions were performed in 20 μl of 25 mM ammonium acetate buffer (pH 6.0) with 30% acetone containing 3 nmol $Man_9GlcNAc_2Asn$, 0.88 mU enzyme and the designated acceptor at 37° C. for 15 min. The analyses were by HPAEC using 100 mM NaOH with a linear gradient of NaOAc increasing from 30 to 80 mM in 30 min.

TABLE 2

Transglycosylation of Man$_9$GlcNAc to GlcNAc glycosides by endo-A.

| Acceptor | Concentration[a] (M) | Yield[b] of hydrolysis (%) | transglycosylation (%) | Transglycosylation index[c] (%) |
|---|---|---|---|---|
| GlcNAc | 0.2 | 4.1 | 84.7 | 95.4 |
| Bn-GlcNAc | 0.05 | 15.0 | 66.7 | 81.6 |
| 4mU-GlcNAc | sat.[d] | 19.9 | 65.5 | 76.7 |
| pNP-GlcNAc | sat. | 45.8 | 32.8 | 41.7 |
| GlcNAc—O—(CH$_2$)$_6$NH$_2$ | 0.2 | 6.5 | 81.1 | 92.6 |
| GlcNAc—O—CH$_2$CH=CH$_2$ | 0.2 | 1.2 | 80.8 | 98.5 |
| GlcNAc—O—(CH$_2$)$_3$CH=CH$_2$ | 0.2 | 9.8 | 83.6 | 89.5 |
| GlcNAc—O—(CH$_2$)$_3$NHCOCH=CH$_2$ | 0.2 | 20.2 | 69.8 | 77.6 |
| GlcNAc—S—CH$_2$CN | 0.2 | 11.3 | 83.4 | 88.1 |
| GlcNAc—S—(CH$_2$)$_3$CH$_3$ | 0.2 | 12.4 | 77.5 | 86.2 |
| (GlcNAc—S—CH$_2$CH$_2$CH$_2$)$_2$ | sat. | 42.0 | 42.6 | 50.4 |
| GlcNAc—S—CH$_2$CONHCH$_2$CH(OMe)$_2$ | 0.2 | 4.0 | 81.0 | 95.3 |

[a] Concentration of the acceptor.
[b] Yield based on the starting substrate.
[c] Percentage of the transglycosylation product in the total digested substrate.
[d] sat.: saturated solution.

Because of the low solubility, the concentration of benzyl β-GlcNAc used was 0.05M, and 4 mU B-GlcNAc and pNP β-GlcNAc were used under saturating conditions (below 0.05M). Even at these concentrations, the enzyme could transfer 67%, 66% and 33%, respectively, of the starting oligosaccharide chain to them and the transglycosylation indices (the percentage of transglycosylation product to digested substrate) were found to be 82%, 77% and 42%, respectively. The thio-glycosides of GlcNAc are good acceptors for Endo-A transglycosylation. When GlcNAc-S-CH$_2$CN, GlcNAc-S(CH$_2$)$_3$CH$_3$ and GlcNAc-S-CH$_2$CONHCH$_2$CH(OMe)$_2$ were used as acceptors at 0.2M, the transglycosylation indices were 88%, 86% and 95%, with yields of 83%, 78% and 81%, respectively. A divalent thio-glycoside of GlcNAc, (GlcNAc-S-CH$_2$CH$_2$CH$_2$)$_2$, could be also used as acceptor for Endo-A transglycosylation at low concentratiou (below 0.05M) with 50% transglycosylation index and 43% yield.

Optimization of the reaction conditions for a larger scale transglycosylation by Endo-A.

Figure 1A:
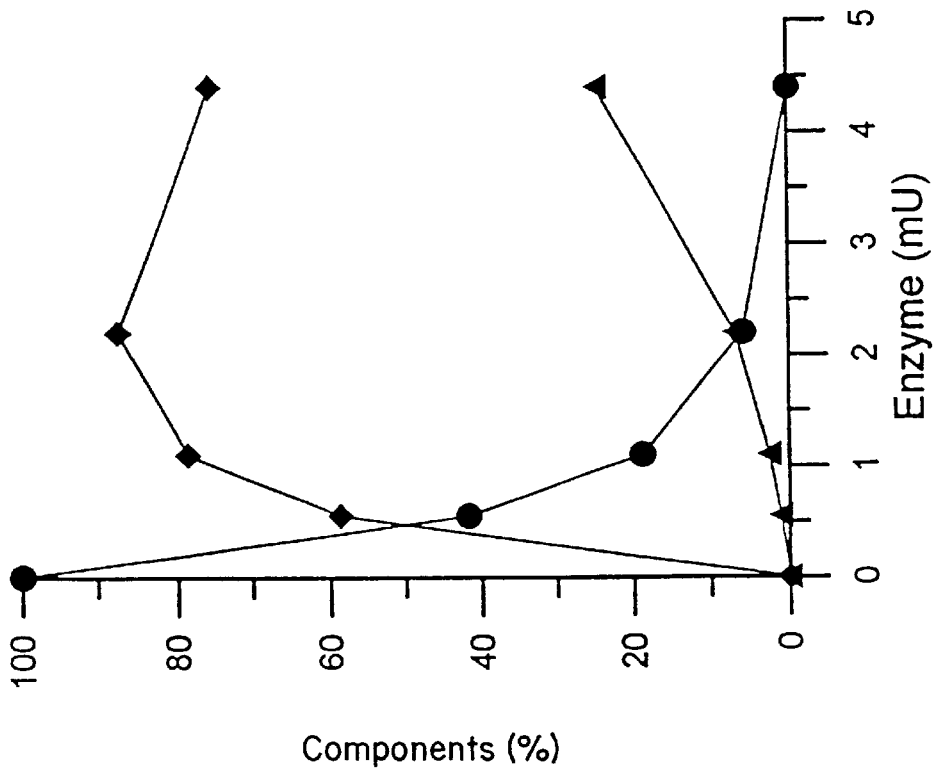

In order to perform the transglycosylation on a larger scale, optimum levels of the enzyme and acetone content were examined for the transglycosylation at higher concentrations of substrate. As shown in FIG. 1A, the hydrolytic product increased in proportion to the amount of enzyme. The yield of transglycosylation product increased upon addition of the enzyme up to 2.2 mU, then decreased as more enzyme was added. When 2.2 mU of enzyme was used, only 5.6% substrate remained. On the other hand, the transglycosylation product increased and the hydrolytic product decreased as the acetone content was increased up to 35% (FIG. 1B). In 35% acetone, 86% transglycosylation and 7% hydrolysis were observed by HPAEC analysis. Although no hydrolytic product was found in the 40% acetone medium, the efficiency of the reaction was lower compared with those in other media, because a greater amount of the substrate (64% of starting substrate) remained.

Synthesis of Man$_9$GlcNAc$_2$-NAP by transglycosylation activity of Endo-A.

Figure 2:
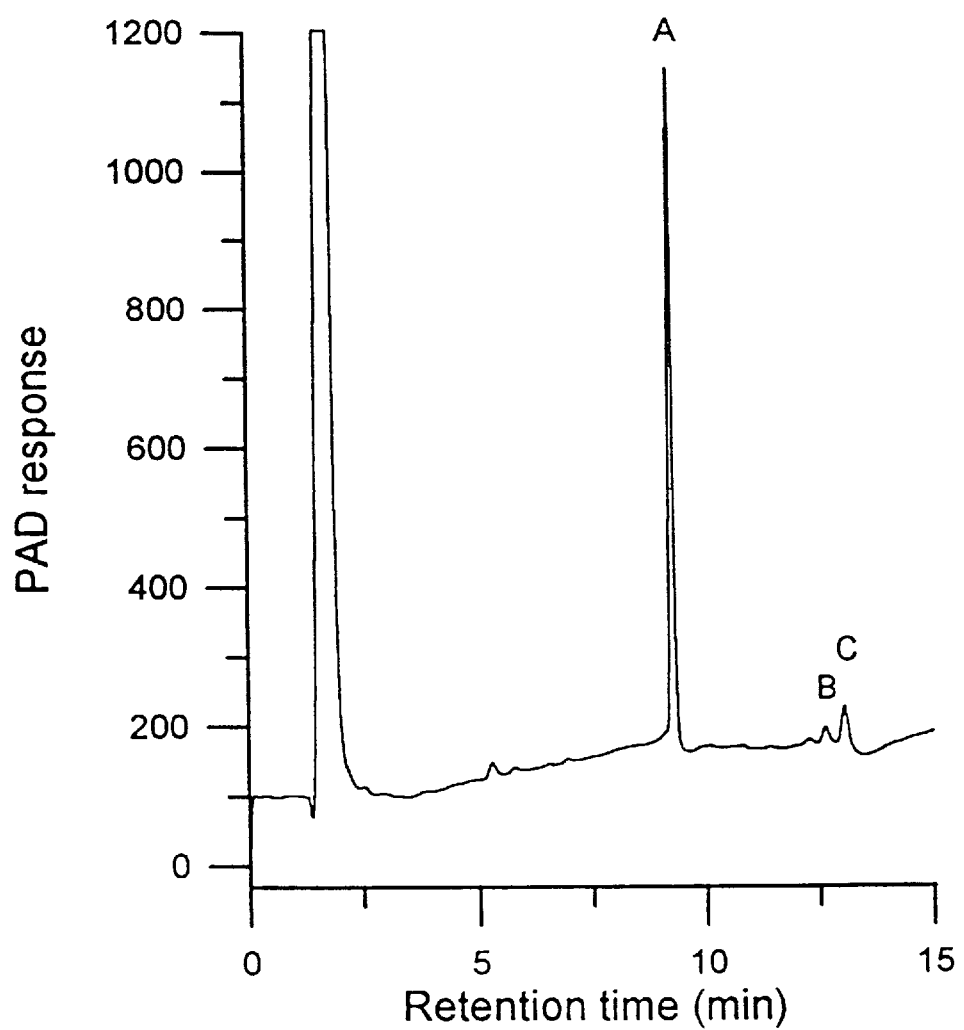
FIG. 2. Synthesis of $Man_9GlcNAc_2$-NAP by Endo-A transglycosylation. The reaction was with 5.75 μmol $Man_9GlcNAc_2Asn$, 2 mmol GlcNAc-NAP and 1.1 U of the enzyme in 5 ml of 10 mM ammonium acetate buffer (pH 6.0) containing 35% acetone at 37° C. for 15 min. After lyophilization, a sample equivalent to 0.7 nmol of $Man_9GlcNAc_2$ oligosaccharide was injected into the HPAEC-PAD system for analysis. The elution was performed with 100 mM NaOH and a linear gradient of NaOAc: 0 to 10% in 20 min. A: transglycosylation product, $Man_9GlcNAc_2$-NAP; B: hydrolytic product, Man9GlcNAc; C: remaining substrate, $Man_9GlcNAc_2Asn$.

To prepare Man$_9$GlcNAc$_2$-NAP in a quantity useful for polymerization, the reaction scale was raised 500-fold over that in the optimum conditions described above. Transglycosylation product, Man$_9$GlcNAc$_2$-NAP, was more than 90% by HPAEC (FIG. 2), and the hydrolysis product as well as the starting donor substrate were barely detected. The unreacted acceptor was recovered by gel filtration on a Sephadex G-25 column and the Man$_9$GlcNAc$_2$-NAP was analyzed by $^1$H-NMR analysis and used for polymerization without further purification.

Figure 3A:
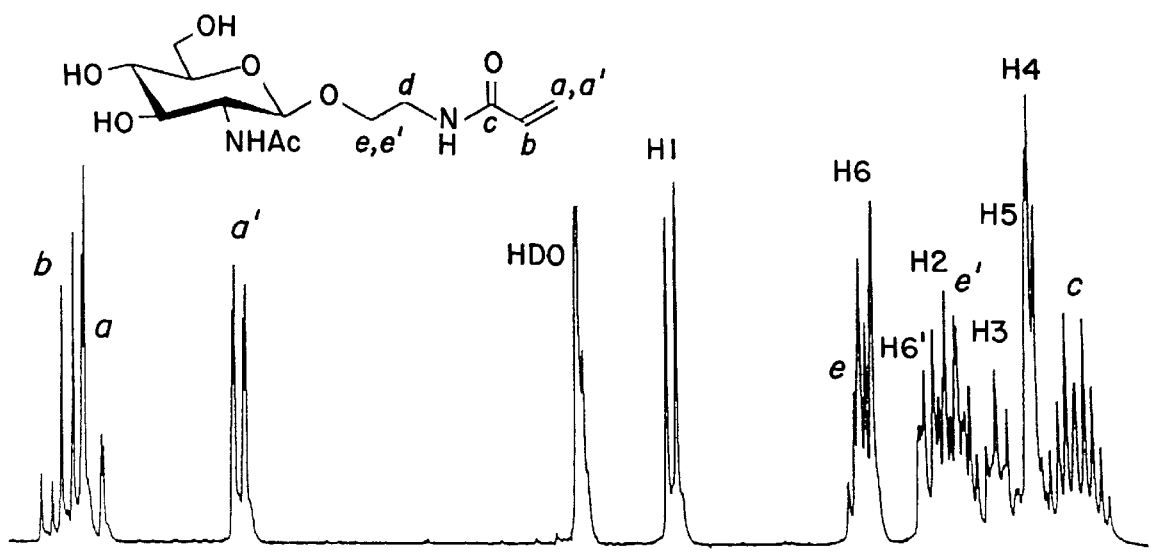
FIGS. 3A and 3B. $^1$H-NMR (300 MHz) Analysis of GlcNAc-NAP (A) and $Man_9GlcNAc_2$-NAP (B). The labile hydrogens in sample were exchanged with deuterium by repeating a cycle of dissolving in $D_2O$ followed by lyophilization three times before measurement. The analyses were done in $D_2O$ using acetone (2.225 ppm) as internal standard at 25° C.

$^1$H-NMR was used to indentify the transglycosylation product. As shown in FIG. 3A, the signals of the acceptor were completely assigned by the decoupling technique. The H-4 signal of GlcNAc was found at 3.436 ppm and the anomeric proton signal was around 4.495 ppm. On the other hand, the $^1$H-NMR analysis of the transglycosylation product showed ten new anomeric proton signals, suggesting that the high mannose type sugar chain was transfered to the acceptor. The $^1$H-NMR assignments based on the reference values (Vliegenthart et al., 1983) are listed in Table 3. The $^1$H-NMR data for GlcNAc-NAP and Man$_9$GlcNAc$_2$-NAP were recorded on a 300 MHz spectrometer in D$_2$O at 25° C. using acetone as internal standard (δ=2.225 ppm). The chemical shifts of Man$_9$GlcNAc$_2$-polymer were recorded on a 600 MHz spectrometer in D$_2$O at 60° C. and relative to HDO (δ=4.441 ppm).

TABLE 3

$^1$H-NMR Data of GlcNAc-NAP, Man$_9$GlcNAc$_2$-NAP and the glycopolymer having Man$_9$GlcNAc$_2$ pendant chains.

| Residue No.[a] | Man$_9$GlcNAc$_2$-Asn[b] | GlcNAc-NAP | Man$_9$GlcNAc$_2$-NAP | Man$_9$GlcNAc$_2$-polymer |
|---|---|---|---|---|
| H-1 of 1 | 5.092 | 4.495 | 4.475 | 4.510 |
| 2 | 4.610 | — | 4.579 | 4.611 |
| NAc of 1 | 2.015 | 2.032 | 2.021 | 2.041 |
| 2 | 2.067 | — | 2.060 | 2.070 |
| H-1 of 3 | ~4.77 | — | 4.744 | 4.763 |
| 4 | 5.334 | — | 5.324 | 5.322 |
| 4' | 4.869 | — | 4.859 | 4.874 |
| A | 5.404 | — | 5.395 | 5.379 |
| B | 5.143 | — | 5.135 | 5.122 |
| C | 5.308 | — | 5.300 | 5.290 |
| D$_1$ | 5.049 | — | 5.034 | 5.057 |
| D$_2$ | 5.061 | — | 5.034 | 5.073 |
| D$_3$ | 5.042 | — | 5.034 | 5.057 |
| CH of a | — | 6.163 | 5.739 | 1.701 |

TABLE 3-continued

1H-NMR Data of GlcNAc-NAP, Man$_9$GlcNAc$_2$-NAP and
the glycopolymer having Man$_9$GlcNAc$_2$ pendant chains.

| Residue No.[a] | Man$_9$GlcNAc$_2$-Asn[b] | GlcNAc-NAP | Man$_9$GlcNAc$_2$-NAP | Man$_9$GlcNAc$_2$-polymer |
|---|---|---|---|---|
| a' | — | 5.748 | 6.161 | 1.701 |
| b | — | 6.278 | 6.262 | ~2.307 |
| c | — | 3.301 | 3.291 | 3.136 |
| d | — | 1.802 | 1.791 | ~1.701 |
| e | — | 3.944 | u.k.[c] | u.k. |
| e' | — | 3.630 | u.k. | u.k. |

Figure 3B:
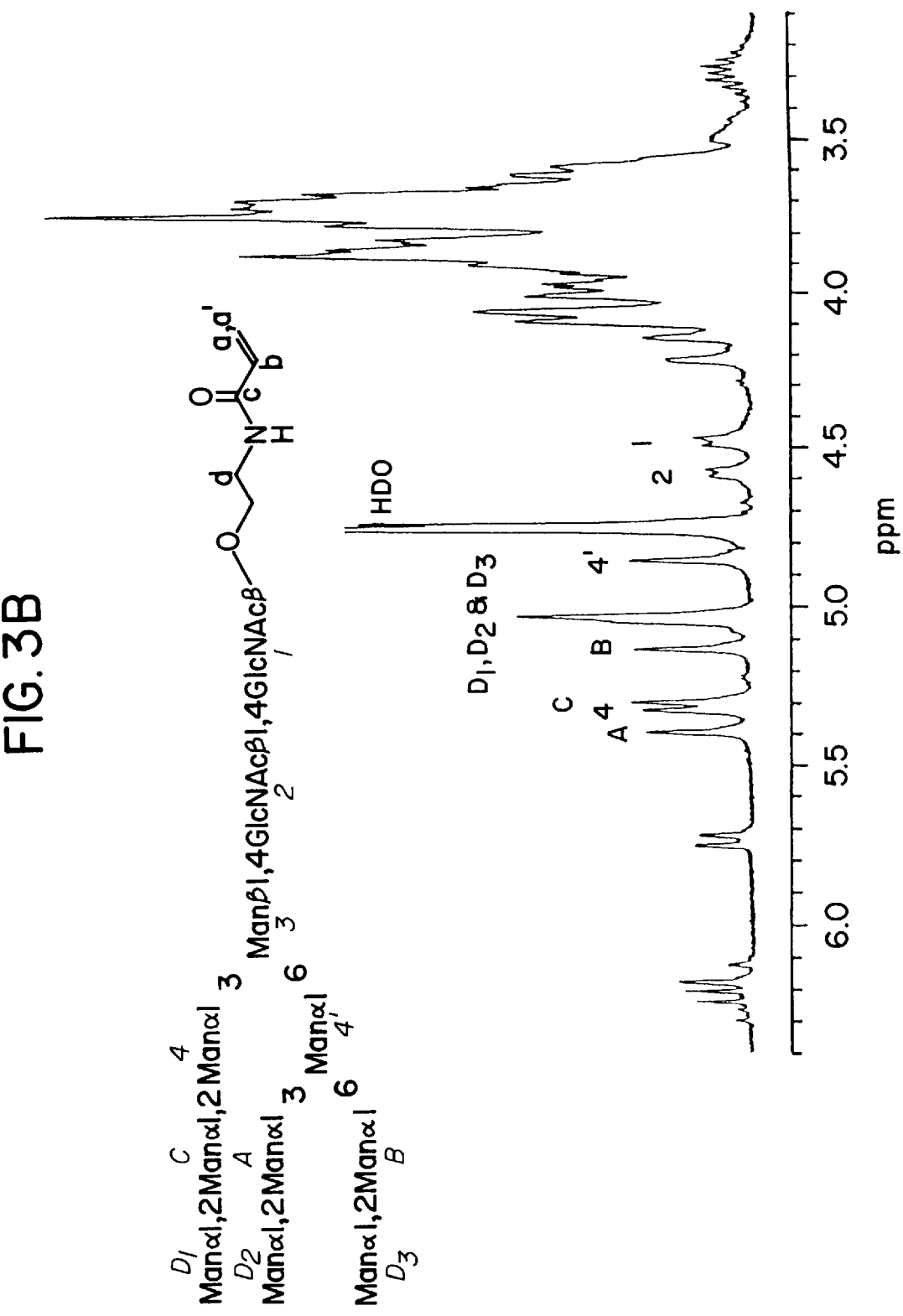

[a]The number were the same as described in FIG. 3
[b]Cited from the published report (17).
[c]u.k.: Unknown.

The anomeric signals agreed with those found from Man$_9$GlcNAc$_2$Asn except two GlcNAc anomeric protons which appeared at higher field than those from the reference compound. This is because the linkages between GlcNAc and the aglycon in the former is an N-amide bond, and in the latter, an O-glycosidic bond. The coupling constant of GlcNAc-2 anomeric proton was 7.8 Hz, indicating that the linkage newly formed by Endo-A transglycosylation is in the β-configuration. The H-4 signal of GlcNAc at the "reducing end" at 3.436 ppm could no longer be seen, in agreement with results obtained with methyl α-GlcNAc and indicating that the linkage occurs at the 4-OH of the GlcNAc. Mass spectrometry analysis showed the expected molecular weight of the transglycosylation product.

Polymerization of Man$_9$GlcNAc$_2$-NAP with acrylamide.

Figure 4:
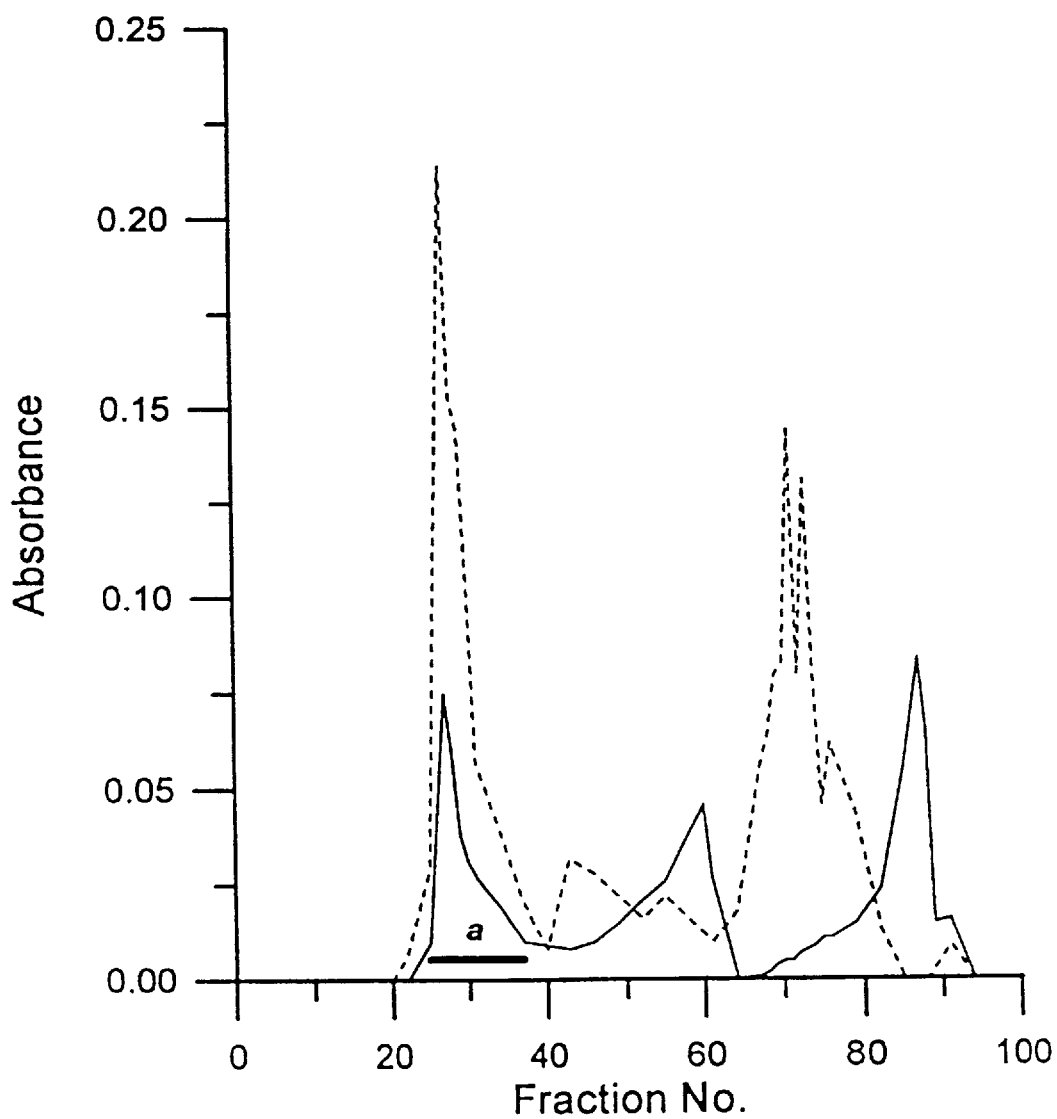
FIG. 4. Gel filtration of the glycopolymer on Sephadex G-50. The sample (1 ml) was applied onto a Sephadex G-50 column (2.5×90 cm), and eluted with water. The flow rate was approximately 30 ml/hr, and 4 ml fractions were collected. The neutral sugar was determined by the phenol-$H_2SO_4$ method (dotted line, absorbance at 480 nm), and GlcNAc was monitored by the absorbance at 220 nm (solid line). a: Indicates the fractions combined as the glycopolymer.
Figure 5:
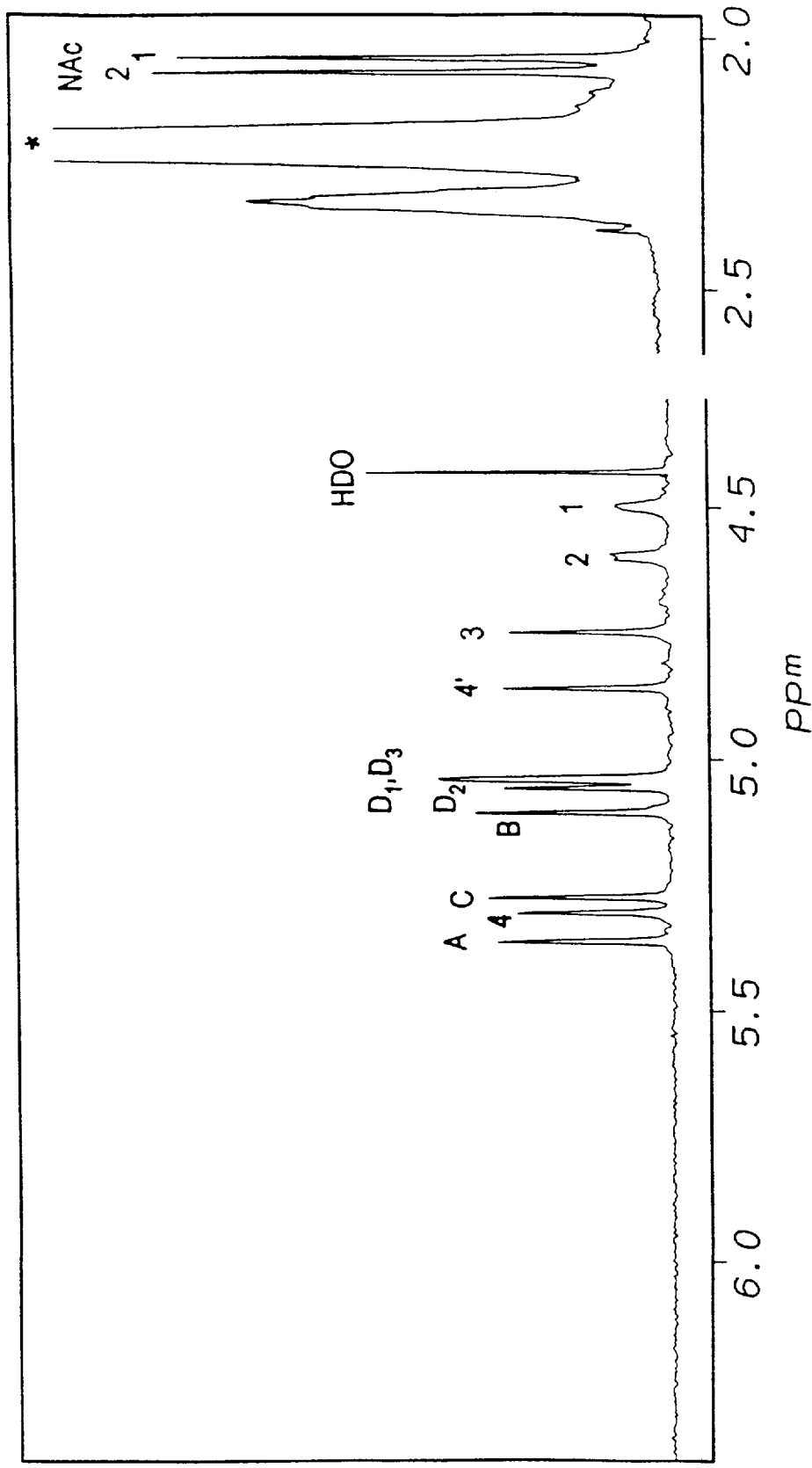
FIG. 5. $^1$H-NMR (600 MHz) Analysis of the glycopolymer. The chemical shifts measured in $D_2O$ at 60° C. were based on the HDO signal at 4.441 ppm. *: Denotes the signals from the polymer back bone.
Figure 6:
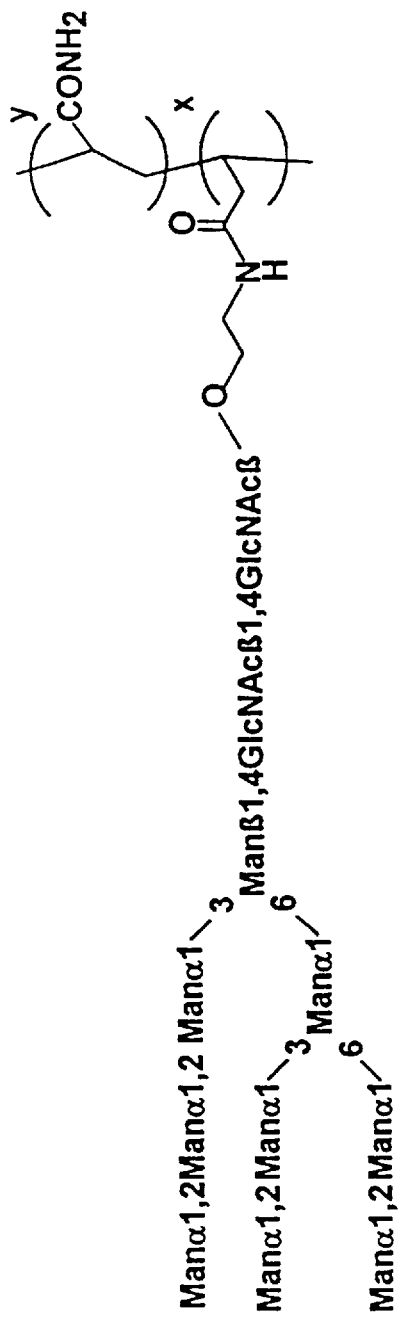
FIG. 6. Glycopolymer having $Man_9GlcNAc_2$ sugar chain.

A glycopolymer was obtained from Man$_9$GlcNAc$_2$-NAP and acrylamide using TEMED and ASP as catalysts. The fractions containing the polymer eluted at the void volume of the Sephadex G-50 column (FIG. 4) were pooled and lyophilized. Completion of the polymerization was indicated by $^1$H-NMR analysis (FIG. 5) which revealed disappearance of the signals at 6.2 ppm and 5.7 ppm, attributable to the unsaturated bond of the aglycon and the acrylamide monomer. The NMR also showed the existence of 11 anomeric proton signals, and the chemical shifts were similar to those found from the monomer (Table 3), confirming that the polymer contains Man$_9$GlcNAc$_2$-sugar chains. The sugar content of the polymer was estimated to be 37% by the phenol-H$_2$SO$_4$ method using mannose as standard. Therefore, the ratio of sugar side chains to acrylamide residues is estimated to be 1:44 as shown in FIG. 6.

Other compounds having a double bond at the terminal position (e.g. GlcNAc-O-CH$_2$CH=CH and other representative compounds shown in Table 2) can be polymerized in essentially the same way. In addition to acrylamide, other monomers (including, for example, styrene derivatives, vinyl, epoxide and ethylenimine type compounds and other compounds with unsaturated bonds) can also be polymerized. As anyone of ordinary skill in the art will appreciate, the polymers resulting from polymerization of these monomers will have backbones consisting of alkylene units (acrylamide, styrene, vinyl) which may optionally contain heteroatoms between said alkylene units (epoxide, ethyleneimine).

Determination of the molecular weight of the glycopolymer

The molecular weight of the glycopolymer was estimated by HPGFC using blue dextran, B-amylase. alcohol dehydrogenase, bovine serum albumin and carbonic anhydrase as reference compounds. The polymer appeared near the void volume, and the retention volume was slightly greater than blue dextran (molecular weight=2,000,000). According to the calibration curve (FIG. 7), the molecular weight is between 1,500,000 and 2,000,000.

Inhibition of mannose-binding proteins by the glycopolymer.

A solid-phase binding assay was carried out on serum- and liver-MBP-CRDs, using the Man$_9$GlcNAc$_2$glycopolymer and soybean agglutinin (SBA), which contains the same Man$_9$GlcNAc$_2$. The results of the assay are shown in FIG. 8. In the concentration range of SBA tested, no significant inhibition of the serum-MBP-CRD was observed. For the liver-MBP-CRD, however, an I$_{50}$ value of 13.2 μM based on Man$_9$GlcNAc$_2$ or 0.4 mg/ml of SBA was obtained. However, the glycopolymer showed an I$_{50}$ of 3.5 μM for the serum-MBP-CRD, and an I$_{50}$ of 74.5 nM for the liver-MBP-CRD. In terms of the whole glycopolymer, the I$_{50}$ values would be approximately 2.0× 10$^{-2}$ mg/ml for the serum-MBP-CRD and 3.8×10$^{-4}$ mg/ml for the liver-MBP-CRD, respectively. The magnitude of inhibitory potency enhancement of the glycopolymer over the precursor cannot be calculated with certainty for the serum form of MBP-CRD, because Man$_9$GlcNAc$_2$ hardly inhibits this MBP-CRD. However, for the liver form, an enhancement was about 180-fold based on the Man$_9$GlcNAc$_2$, and ca. 1,000-fold based on the moleculars, although the sugar content of the glycopolymer was only 5.6-fold higher than SEA.

DISCUSSION

Endo-A demonstrates an efficient transglycosylation activity (>90%) in 30% acetone, much higher than the 10–30% reported for other glycosidases (Bardales et al., 1989; Sakai et al., 1992; Cantacuzene et al., 1991; Nilsson, 1987 and 1989; Usui and Murata, 1988; and Usui et al., 1994). This finding has been utilized to synthesize neoglycoconjugate intermediates which are amenable to further reactions.

Endo-A also transfers Man$_9$GlcNAc to alcohols such as MeOH, EtOH and PrOH. The transglycosylation to MeOH (64% yield) and EtOH (47% yield) compares favorably with those by β-xylosidase, α- and β-glucosidase and β-galactosidase (20–60%) from various sources (Shinoyama et al., 1988; and Shinoyama and Yasai, 1988). However, transglycosylations to PrOH and iPrOH were not as effective as to MeOH and EtOH. Interestingly, although the total enzyme activity was lower in PrOH than in iPrOH, transglycosylation to PrOH was greater than to iPrOH. Glycerol was also a good acceptor for Endo-A transglycosylation. Endo-B-N-acetylglucosaminidase F (Trimble et al., 1986) and Endo-α-N-acetylgalactosaminidase from *Diplococcus pneumoniae* (Bardales and Bhavanandan, 1989) have been reported to transfer an oligosaccharide to the C1(3) hydroxyl of glycerol.

Several GlcNAc derivatives having functionalized aglycons useful for synthesis of neoglycoconjugates were tested as acceptors for Endo-A transglycosylation. The yields based on the starting donor substrate were found to be greater than 80% with 0.2M acceptor and about 50% when 0.05M or less was used in our system. The yield of transglycosylation can be further improved if higher acceptor concentrations are employed.

Endo-A transglycosylation is also effective at higher concentrations of reactants, as shown in Table 2. In the larger-scale transglycosylation to GlcNAc-NAP, transglycosylation yield (>90%) was even higher than those at the analytical scale reaction. A similar yield (89%) can be obtained from the transglycosylation to GlcNAcα-OMe on a similar scale (4 μmol).

An Endo-A transglycosylation product, Man$_9$GlcNAc$_2$-NAP, was further polymerized with acrylamide to form a glycopolymer. Glycopolymers having di- or trisaccharide have been synthesized by chemical or chemo-enzymatic method recently (Kochetkov, 1984; Nishimura et al, 1991; Nishimura et al., 1994a and 1994b; Kobayashi et al., 1994; and Fukase et al., 1994), but to our knowledge this is the first time glycopolymers with highly complex sugar chains have been synthesized. The high efficiency of Endo-A transglycosylation provides an easier way to synthesize such neoglycoconjugates.

Clustering of monosaccharides by attachment to a simple branched peptides enhances inhibitory potencies for some C-type lectins (Lee and Lee, 1987; and Lee et al., 1992). An affinity enhancement achieved by multivalent ligands over monovalent ones that is greater than would be expected from a simple effect of a local concentration increase is termed the "glycoside cluster effect". Formation of glycopolymers is convenient way to provide glycoside clustering (Lee and Lee, 1994). In the instant invention, a dramatic increase in the inhibition of MBP-CRDs in comparison with that by the native glycoprotein (SBA) which contains the same Man$_9$GlcNAc$_2$ oligosaccharide is demonstrated. In the case of the liver MBP-CRD, an approximately 180-fold enhancement of inhibitory potency over the native glycoprotein (SBA) was attained by the glycopolymer. Similarly, although no significant inhibition of the serum MBP-CRD was observed for SBA, the glycopolymer derived from its oligosaccharide demonstrated a surprisingly strong inhibitory potency ($I_{50}$=3.5 μM). This is a good example of "macro-" vs. "micro-clustering" (Lee, 1993). ["Microclustering" describes a condition where the spatial arrangement of the target sugars is such that the distances between combining sites are small—e.g. 1.5 to 3.0 nM; "macrocluster" describes a condition where the spatial arrangement is such that the distances are much greater (e.g. 50–100 nM, as here)]

It will be apparent that the compounds described herein have many potential uses. In addition to their utility in the study of carbohydrate function and metabolism, the various compounds may also be used for diagnostic and therapeutic purposes, for example as antigens or for the measurement or isolation of specific carbohydrate binding proteins.

Measurement of MBP in a serum sample

MBP is one of the acute phase proteins produced by liver in response to invading microorganisms or other foreign agents (Reid, 1983, Sastry et al., 1991). MBP binds to these agents, leading to their destruction either directly or through the participation of macrophages. The Man$_9$GlcNAc$_2$ glycopolymer of the present invention has a much greater binding affinity than natural products containing mannose, and should thus be useful for diagnosis in a manner similar to that of C-reactive protein (Oyamada et al, 1992; Ohtake, 1993).

To measure the amount of MBP in a serum sample, the following procedure can be used:

1) The Man$_9$GlcNAc$_2$ glycopolymer of FIG. 6 is conjugated to an enzyme commonly used for ELISA assays, for example alkaline phosphatase or β-galactosidase.

2) A monoclonal antibody against MBP which does not affect its ability to bind mannose is placed in a well to coat its surface. Such antibodies can be made using standard techniques known to the skilled practitioner, for example as described by Quesenberry and Drickamer (1992). A sample of serum to be tested is placed in the coated well and incubated under conditions favorable for binding of MBP to the antibody.

3) The unbound material is removed by suitable washing, and the glycopolymer-phosphatase complex of (1) is placed in the well. The MBP bound to the antibody now binds the glycopolymer, acquiring the phosphatase activity. Upon addition of a suitable substrate, the level of phosphatase activity is a measure of the MBP in the serum sample.

Alternatively, the well can be coated with the unconjugated glycopolymer, the serum sample added, and bound MBP reacted with anti-MBP conjugated to phosphatase or another suitable enzyme. The level of MBP can then be determined, as before, by the bound enzymatic activity.

The references earlier mentioned are more fully identified hereafter, and are hereby incorporated by reference and relied upon:

Bardales, R. M., and Bhavanandan, V. P. (1989) *J. Biol. Chem.* 264, 19893–19897.

Cantacuzene, D., Attal, S., and Bay, S. (1991) *Biomed. Biochim. Acta* 50, S231–S236.

De Lean, A., Munson, P. J. and Rodbard, D. (1978) *Am. J. Physiol.* 235, E97–E102.

Fan. J.-Q., Kondo, A., Kato, I., and Lee, Y. C. (1994) *Anal. Biochem.* 219, 224–229.

Fukase, K., Nakayama, H., Kurosawa, M., Ikegaki, T., Kanoh, T., Hase, S., and Kusumoto, S. (1994) *J. Carbohydr. Chem.* 13, 715–736.

Glick, G. D., Toogood, P. L., Wiley, D. C., Skehel, J. J., and Knowles, J. R. (1991) *J. Biol. Chem.* 266, 23660–23669.

Kobayashi, K., Kakishita, N., Okada, M., Akaike, T., and Usui, T. (1994) *J. Carbohydr. Chem.* 13, 753–766.

Kochetkov, N. K. (1984) *Pure & Appl. Chem.* 56, 923–938.

Lasky, L. A. (1992) *Science* 258, 964–969.

Lee, Y. C. (1988) in "The Molecular Immunology of Complex Carbohydrates", (Wu, A. M., Ed.), Series Plenum Publishing Corporation, pp. 105–121.

Lee, Y. C. (1993) *Biochem. Soc. Trans.* 21, 460–463.

Lee, Y. C. (1994) in "Neoglycoconjugates: Preparation and Applications" (Lee, Y. C. and Lee, R. T., Eds) Academic Press, San Diego, pp. 3–21.

Lee, R. T., Ichikawa, Y., Kawasaki, T., Drickamer, K. and Lee, Y. C. (1992) *Arch. Biochem. Biophys.* 299, 129–136.

Lee, R. T., Ichikawa, Y., Fay, M., Drickamer, M. C., Shao, M. C., and Lee, Y. C. (1991) *J. Biol. Chem.* 266, 4810–4815.

Lee, R. T. and Lee, Y. C. (1987) *Methods Enzymol.* 138, 424–429.

Lee, Y. C., and Lee, R. T. (1992) in "Glycoconjugates: Composition, Structure, and Function" (Allen, H. J., and Kisalius, E. C., Eds.), Marcel Dekker, Inc., New York, pp. 121–165.

Lee, R. T., and Lee, Y. C. (1994) in "Neoglycoconjugates: Preparation and Applications" (Lee, Y. C. and Lee, R. T., Eds.) Academic Press, San Diego, pp. 23–50.

Lee, Y. C., Lee, R. T., Rice, K., Ichikawa, Y., and Wong, T.-C. (1991) *Pure & Appl. Chem.* 63, 499–506.

McKelvy, J. F., and Lee, Y. C. (1969) *Arch. Biochem. Biophy.* 132, 99–110.

Nilsson, K. G. I. (1987) *Carbohydr. Res.* 167, 95–103.

Nilsson, K. G. I. (1989) *Carbohydr. Res.* 188, 9–17.

Nishimura, S., Furuike, T., Matsuoka, K., Murayama, S., Nagata, K., Kurita, K., Nishi, N., and Tokura, S. (1994a) *Macromolecules* 27, 4876–4880.

Nishimura, S., Matsuoka, K., Furuike, T., Ishii, S., Kurita, K., and Nishimura, K. M. (1991) *Macromolecules* 24, 4236–4241.

Nishimura, S., Matsuoka, K., and Kurita, K. (1990) *Macromolecules* 23, 4182–4184.

Nishimura, S., Matsuoka, K., Furuike, T., Nishi, N., Tokura, S., Nagami, K., Murayama, S., and Kurita, K. (1994b) *Macromolecules* 27, 157–163.

Ohtake, T. (1993) *Med. Technol.* 721, 287–293.

Oyamada, H., Nakagomi, O., and Usugi, S. (1992) *Jap. J. Clin. Path.* 40, 9–15.

Patankar, M. S., Oehninger, S., Barnett, T., Williams, R. L., and Clark, G. F. (1993) *J. Biol. Chem.* 268, 21770–21776.

Quesenberry, M. S. and Drickamer, K. (1992) *J. Biol. Chem.* 267, 10831–10841.

Reid, K. B. M. (1983) *Biochem. Soc. Trans.* 11, 1–12.

Sakai, K., Katsumi, R., Ohi, H., Usui, T, and Ishido, Y. (1992) *J. Carbohydr. Chem.* 11, 553–565.

Sastry, K, Sahedi, K., Lelias, J.-M., Whitehead, A. S. and Ezkowitz, R. A. B. (1991) *J. Immunol.* 147: 692–697.

Shinoyama, H., Kamiyama, Y., and Yasui, T. (1988) *Agric. Biol. Chem.* 52, 2197–2202.

Shinoyama, H., and Yasui, T. (1988) *Agric. Biol. Chem.* 52, 2375–2377.

Stowell, C. P., and Lee, Y. C. (1993) In "Methods in Carbohydrate Chemistry, Vol. IX", (J. N. BeMiller, R. L. Whistler, and D. H. Shaw, eds.) Wiley & Sons, Inc., pp. 173–178.

Takegawa, K., Nakoshi, M., Iwahara, S., Yamarnoto, K., and Tochikura, T. (1989) *Appl. Environ. Microbiol.* 55, 3107–3112.

Takegawa, K., Tabuchi, M., Yamaguchi, S., Kondo, A., Kato, I., and Iwahara, S. (1995) *J. Biol. Chem.* 270, 3094–3099.

Takegawa, K., Yamaguchi, S., Kondo, A., Iwamoto, H., Nakoshi, M., Kato, I., and Iwahara., S. (1991a) *Biochem. Int.* 24, 849–855.

Takegawa, K., Yamaguchi, S., Kondo, A., Kato, I., and Iwahara, S. (1991b) *Biochem. Int.* 25, 829–835.

Toogood, P. L., Galliker, P. K., Glick, G. D., Knowles, J. R. (1991) *J. Med. Chem.* 34, 3140–3143.

Trimble, R. B., Atkinson, P. H., Tarentino, A. L., Plummer, T. H., Jr., Maley, F., and Tomer, K. B. (1986) *J. Biol. Chem.* 261, 12000–12005.

Usui, T., and Murata, T. (1988) *J. Biochem.* 103, 969–972.

Usui, T., Suzuki, M., Sato, T., Kawagishi, H., Adachi, K., and Sano, H. (1994) *Glycoconjugate J.* 11, 105–110.

Vliegenthart, J. F. G., Dorland, L, and van Halbeek, H., (1983) *Adv. Carbohydr. Chem. Biochem.* (Tipson, R. S., and Horton, D., Eds.), Vol. 41, pp. 209–373.

Wassarman, P. M. (1991) *Development* 108, 1–17.

While the invention has been described in connection with what is presently considered to be the most practical and preferred embodiment, it is to be understood that the invention is not to be limited to the disclosed embodiment, but is intended to cover various modifications included within the spirit and scope of the appended claims.

What is claimed is:

1. A glycopolymer that contains high mannose sugar chains and whose synthesis comprises i) combining a donor and an acceptor in a reaction mixture containing Endo-β-N-acetylglucosaminidase from *Arthrobacter protophormiae* and an organic solvent, ii) incubating the reaction mixture to produce a transglycosylation product, iii) purifying said transglycosylation product on a column, and iv) polymerizing said transglycosylation product to produce a polymer having a backbone consisting of alkylene units, which may optionally contain heteroatoms between said alkylene units.

2. The glycopolymer of claim 1 wherein said polymerization employs acrylamide.

3. A glycopolymer having a backbone consisting of alkylene units, which may optionally contain heteroatoms between said alkylene units and pendant $Man_9GlcNAc_2$ chains which inhibits mannose binding protein from the liver in vitro.

4. The glycopolymer shown in FIG. 6 (Diagram 1).

5. A method of synthesizing a glycopolymer containing high mannose sugar chains comprising the steps of i) combining a donor and an acceptor in a reaction mixture containing Endo-β-N-acetylglucosaminidase from *Arthrobacter protophormiae* and an organic solvent, ii) incubating the reaction mixture such that a transglycosylation product is produced, and iii) polymerizing said transglycosylation product to produce a polymer having a backbone consisting of alkylene units, which may optionally contain heteroatoms between said alkylene units.

6. The method according to claim 5 where said glycopolymer is a glycopolymer with pendant $Man_9GlcNAc_2$ chains.

* * * * *